United States Patent [19]
Greengrass

[11] Patent Number: 4,726,373
[45] Date of Patent: Feb. 23, 1988

[54] WIRE GUIDED DILATOR DEVICE

[75] Inventor: Stuart M. Greengrass, Magna, United Kingdom

[73] Assignee: Keymed (Medical & Industrial Equipment) Ltd, Southend-on-Sea, United Kingdom

[21] Appl. No.: 780,150

[22] Filed: Sep. 26, 1985

[30] Foreign Application Priority Data

Sep. 27, 1984 [GB] United Kingdom ............. 8424396

[51] Int. Cl.$^4$ .............................................. A61M 29/00
[52] U.S. Cl. .................................. 128/343; 128/348.1; 128/341
[58] Field of Search ............... 128/341, 343, 348.1, 128/656–658, 756, 772, 207.14, 207.15; 604/104, 170

[56] References Cited

U.S. PATENT DOCUMENTS

| | | | |
|---|---|---|---|
| 3,638,655 | 2/1972 | Doherty | 128/207.15 |
| 3,880,168 | 4/1975 | Berman | 128/207.15 |
| 4,307,722 | 12/1981 | Evans | 128/341 |
| 4,323,071 | 4/1982 | Simpson et al. | 128/343 |
| 4,564,014 | 1/1986 | Fogarty et al. | 128/348.1 |

Primary Examiner—Richard J. Apley
Assistant Examiner—H. Flaxman
Attorney, Agent, or Firm—Beveridge, DeGrandi & Weilacher

[57] ABSTRACT

The dilator has a central bore for a guide wire and a flexible distal portion merging continuously with an intermediate portion of constant cross-section. A proximal portion is convex in profile and merges continuously with the intermediate portion. The distal portion comprises a hemispherical tip followed by a conical section, a concave section and a convex section, respectively. The dilator is primarily for dilating oesophageal strictures when used in conjunction with an endoscope to place the guide wire and is urged along the wire using a threadably engaged insertion rod.

9 Claims, 4 Drawing Figures

WIRE GUIDED DILATOR DEVICE

FIELD OF THE INVENTION

This invention relates to wire guided dilator devices and particularly, though not exclusively, to such devices for dilating oesophageal strictures.

SUMMARY OF THE INVENTION

The invention provides a wire guided dilator device comprising a dilator which has a central bore to accommodate a guide wire, a distal portion and a proximal portion both continuous with an intermediate portion of substantially constant cross-section, the distal portion having a distally decreasing cross-section and the proximal portion having a proximally decreasing cross-section.

Preferably, at least the distal portion is flexible.

The distal portion may be at least partially concave and/or convex in profile. Where there are both concave and convex sections, these may be continuous with one another.

The distal portion may be at least partially conical; where there are conical and concave sections, these may be continuous with one another.

Preferably, the proximal portion is at least partially convex in profile.

For manipulating the dilator in use, the device would typically comprise an insertion rod which would preferably have a cross-section less at any point than the cross-section of the intermediate portion.

DETAILED DESCRIPTION OF THE DRAWINGS

Figure 1:
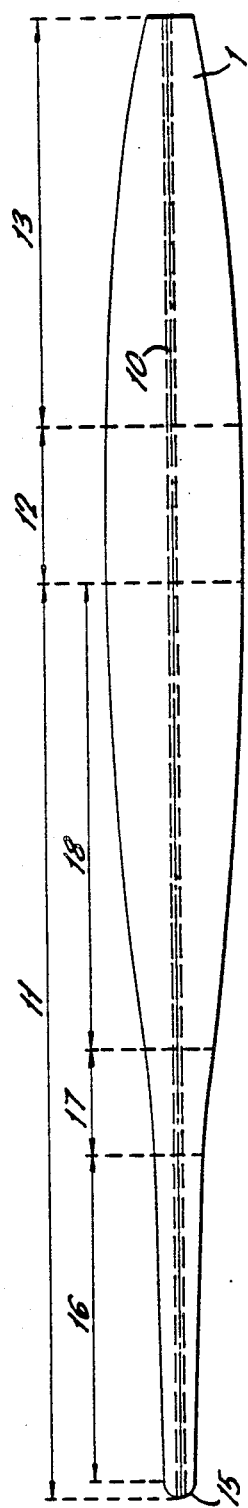
FIGS. 1, 2 and 3 each show in cross-sectional elevation, a different embodiment of a dilator in accordance with the invention.
Figure 2:
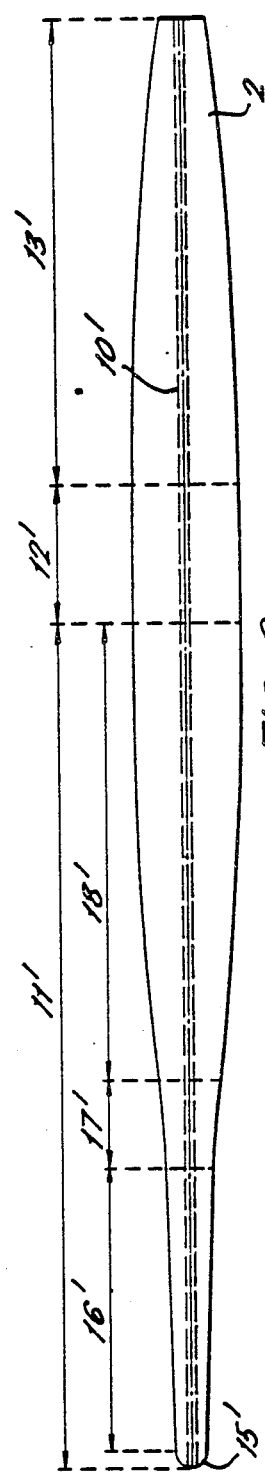
Figure 3:
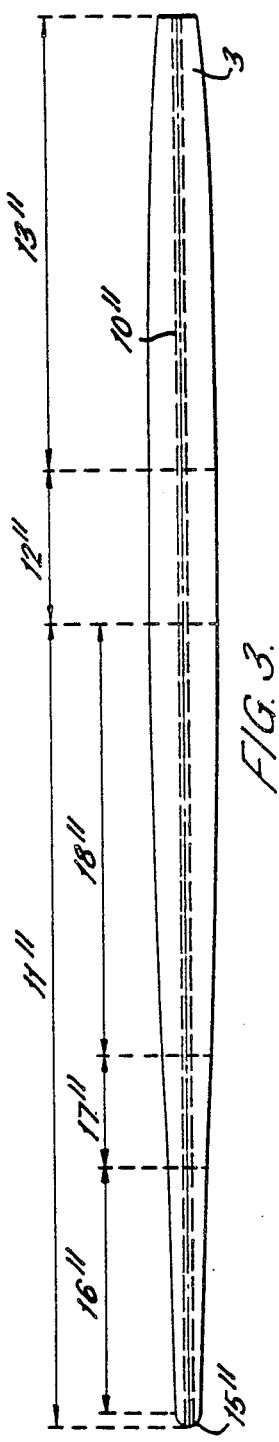
Figure 4:
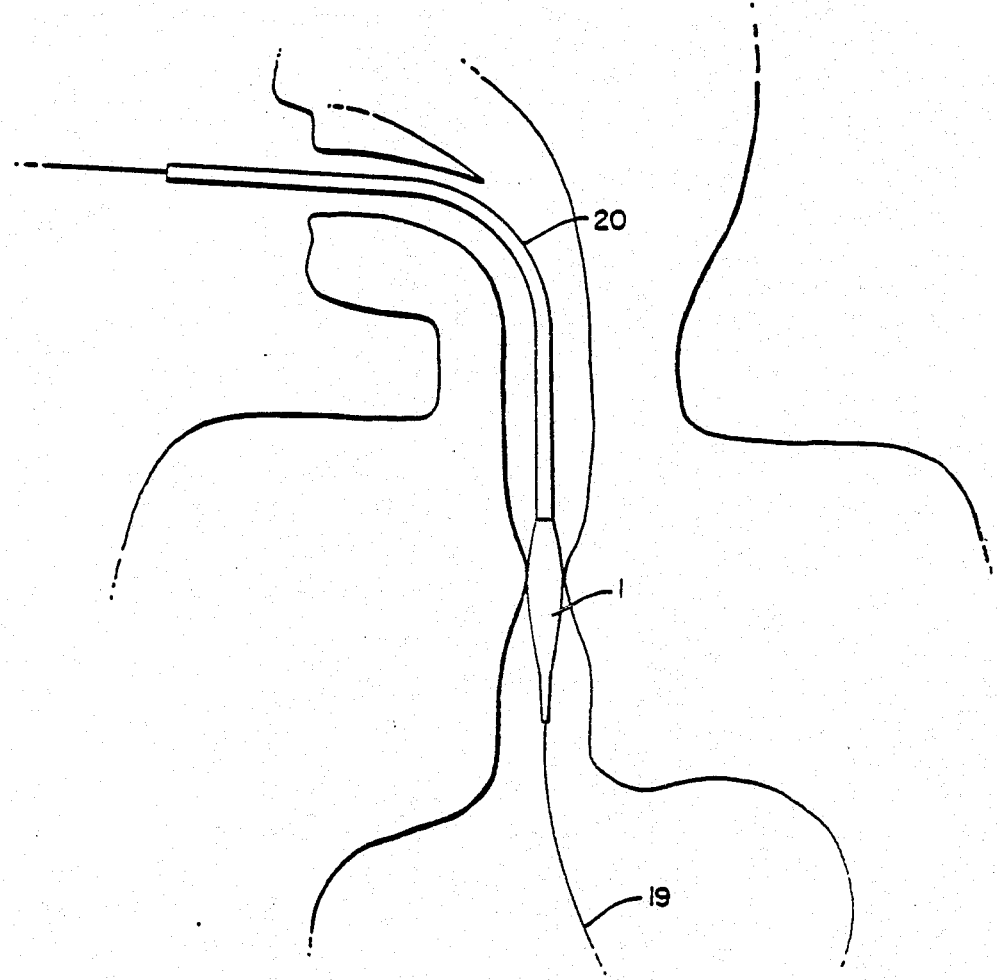
FIG. 4, illustrates the present invention in operation.

Each of the dilators 1, 2, 3 consists of an elongate body formed integrally from a flexible material such as rubber or a suitable plastics material. Each dilator is round in cross-section throughout and is formed with a central bore 10, 10', 10" to accommodate a guide wire as is known in the art.

Each dilator has three basic portions, namely an elongate distal portion 11, 11', 11", an intermediate portion 12, 12', 12" and a proximal portion 13, 13', 13". As can be seen from the drawings, the three portions of each dilator are continuous with one another so as to provide a smooth outer surface of each dilator without bumps or irregularities. The intermediate portion of each dilator is of constant diameter while the cross-section of each proximal portion decreases proximally i.e. away from the intermediate portion. Each proximal portion is convex in profile, that is its diameter decreases with increasing rapidity in the proximal direction. In profile the outer surface of the proximal portion is in fact a circular arc.

The distal portion of each dilator is in four sections: a hemispherical tip 15, 15', 15", a conical section 16, 16', 16", a section 17, 17', 17" which is concave in profile and a section 18, 18', 18" which is convex in profile. Again, adjacent sections are continuous with one another so that the outer surface of the distal portion is smooth and not disjointed. Like each proximal portion, each convex section 18, 18', 18" has a circular arcuate outer profile. Each concave section provides a smooth transition between its respective convex and conical sections.

Each dilator is provided at its proximal end with a screw threaded insert (not shown) concentric with the central bore for threaded engagement with a plastic or spirally wound metal insertion rod 20 in know fashion. Alternatively, the dilator may be permanently attached to the rod and may even be formed integrally therewith. The insertion rod has a diameter less than the diameter of any of the intermediate portions 12, 12', 12". In use for the dilation of oesophageal strictures, the guide wire 19 is passed, via an endoscope, down the oesophagus and through the stricture, after which the endoscope is removed leaving the guide wire in place. The assembly of dilator and insertion rod is then threaded onto the guide wire and advanced carefully down the oesophagus. It will be appreciated that passage of the dilator through the stricture will cause dilation of the stricture to the diameter of the intermediate portion. The choice of dilator (the three dilators illustrated being similar in length but having different diameters) or indeed of dilators of different sizes, will of course depend on the amount of dilation required although it is usual to start with the smallest diameter dilator (3) and continue with sequentially larger dilators.

The dilators described above have numerous and important advantages over previous dilators. The flexibility of the dilator, particularly the distal portion, avoids trauma or difficulty for the patient during use because it bends easily over the crico-pharynx and will negotiate tight or tortuous paths, following the guide wire to give a much safer passage than previous dilators. This flexibility also means that the kinking of guide wires is drastically reduced. The shape of the dilator results in particular effectiveness of dilation resulting from the sequential conical, concave, convex and constant diameter sections of the dilator. The convex proximal portion aids subsequent removal of the dilator, particularly through the crico-pharynx. The dilator device as a whole is simple and mechanically uncomplicated to use and the dilator length is kept to a minimum ensuring that passage can be made safely within a hiatus hernia. The insertion rod may be of small diameter thus reducing trauma to the crico-pharynx and preventing the patient aspirating blood or mucus into his/her lungs, which would result in subsequent complications.

I claim:

1. A wire guided dilator device, comprising:
a dilator having a central bore through which a guide wire extends in use, said dilator comprising a flexible distal portion, a proximal portion and an intermediate portion, said distal, intermediate, and proximal portions each having a smooth outer surface which is continuous with the other two outer surfaces so as to form a smooth, continuous exterior dilator surface, with said intermediate portion of substantially constant cross-section, said proximal portion of proximally decreasing cross-section and said distal portion having a cross-section continuously and distally decreasing to a smooth hemispherical tip,
and said dilator, apart from the bore formed therein, being solid and integrally formed from rubber or plastics material and said intermediate section being essentially non-deformable in cross section such that the passage of the dilator through a stricture will cause the stricture to dilate to conform to the outer periphery of said intermediate portion 2. A device as claimed in claim 1 wherein the distal portion is at least partially concave in profile.

3. A device as claimed in claim 1 wherein the distal portion is at least partially convex in profile.

4. A device as claimed in claim 1 wherein the distal portion includes a concave section being concave in profile and a convex section being convex in profile, which concave and convex sections are continuous with one another.

5. A device as claimed in claim 1 wherein the distal portion is at least partially conical.

6. A device as claimed in claim 4 wherein the distal portion is at least partially conical.

7. A device as claimed in claim 1 wherein the proximal portion is at least partially convex in profile.

8. A device as claimed in claim 1 wherein said distal portion has a conical section merging continuously with said smooth hemispherical tip, a concave section concave in profile and merging continuously with the conical section, and a convex section being convex in profile and merging continuously with the concave section.

9. A device as claimed in claim 1 further comprising an insertion rod, a bore extending centrally and longitudinally through said insertion rod and an end of said insertion rod being connected to the proximal end of said dialator with their respective bores in alignment such that in use said dilator and insertion rod may be threaded onto a guide wire and said dilator advanced along the wire by manipulation of said insertion rod, and said insertion rod having a cross-section which is less over its entire length than the cross-section of the intermediate portion of the dialator.

* * * * *